US007960342B2

(12) United States Patent
Rivier et al.

(10) Patent No.: US 7,960,342 B2
(45) Date of Patent: Jun. 14, 2011

(54) RECEPTOR(SSTR2)-SELECTIVE SOMATOSTATIN ANTAGONISTS

(75) Inventors: Jean E. F. Rivier, La Jolla, CA (US); Judit Erchegyi, San Diego, CA (US); Jean Claude Reubi, Berne (CH); Helmut R. Maecke, Basel (CH)

(73) Assignees: The Salk Institute for Biological Studies, La Jolla, CA (US); Universitat Bern, Bern (CH); University Hospital Basel, Basel (CH)

( * ) Notice: Subject to any disclaimer, the term of this patent is extended or adjusted under 35 U.S.C. 154(b) by 691 days.

(21) Appl. No.: 11/872,367

(22) Filed: Oct. 15, 2007

(65) Prior Publication Data
US 2008/0260638 A1 Oct. 23, 2008

Related U.S. Application Data

(60) Provisional application No. 60/829,637, filed on Oct. 16, 2006.

(51) Int. Cl.
A61K 38/18 (2006.01)
A61K 38/31 (2006.01)

(52) U.S. Cl. ........................................ 514/9.7; 514/11.1
(58) Field of Classification Search ........................ None
See application file for complete search history.

(56) References Cited

U.S. PATENT DOCUMENTS

| 4,428,942 | A |   | 1/1984  | Rivier et al.         |
|-----------|---|---|---------|-----------------------|
| 5,590,656 | A |   | 1/1997  | O'Dorisio et al.      |
| 5,837,218 | A | * | 11/1998 | Peers et al. ... 424/1.69 |
| 5,846,934 | A |   | 12/1998 | Bass et al.           |
| 5,925,618 | A |   | 7/1999  | Baumbach et al.       |
| 6,262,229 | B1|   | 7/2001  | Coy et al.            |
| 6,579,967 | B1|   | 6/2003  | Rivier et al.         |
| 7,019,109 | B2|   | 3/2006  | Rivier et al.         |
| 2002/0137676 | A1 | | 9/2002 | Hsiang et al.         |
| 2004/0242842 | A1 | | 12/2004| Maecke et al.         |
| 2005/0070470 | A1 | | 3/2005 | Coy et al.            |
| 2005/0245438 | A1 | | 11/2005| Rivier et al.         |
| 2006/0089299 | A1 | | 4/2006 | Hsiang et al.         |

FOREIGN PATENT DOCUMENTS

| EP | 0 203 031     | * | 7/1992 |
|----|---------------|---|--------|
| WO | WO97/11962 A1 |   | 4/1997 |
| WO | WO-98/24807 A0|   | 6/1998 |
| WO | WO00/12111    |   | 3/2000 |
| WO | WO-01/44273 A0|   | 6/2001 |
| WO | WO-02/32932 A0|   | 4/2002 |
| WO | WO2004/082722 A2|  | 9/2004 |
| WO | WO-2008/048942|   | 4/2008 |

OTHER PUBLICATIONS

Hirst et al., "Structure-Activity Studies with Somatostatin: the Role of Tryptophan in Position 8", *Regulatory Peptides* (1980), vol. 1, pp. 97-113.

Reubi et al., "Concomitant expression of several peptide receptors in neuroendocrine tumours: molecular basis for in vivo multireceptor tumour targeting", *European Journal of Nuclear Medicine and Molecular Imaging* (2003), vol. 30, No. 5, pp. 781-793.

Schottelius et al., "First 18F-Labeled Tracer Suitable for Routine Clinical Imaging of sst Receptor-Expressing Tumors Using Positron Emission Tomography", *Clinical Cancer Research* (2004), vol. 10, pp. 3593-3606.

Yabe et al., "Synthesis and Biological Activity of Somatostatin Analogues modified at the Tryptophan Residue", *Chem. Pharm. Bull.* (1978), vol. 26, No. 3, pp. 993-997.

International Search Report (PCT/US2009/040672) dated May 11, 2010.

Ginj, et al, "Radiolabeled Somatostatin Receptor Antagonists are Preferable to Agonists for in Vivo Peptide Receptor Targeting of Tumors," Proceedings of the National Academy of Sciences of the United States of America, vol. 103, No. 44, Oct. 2006.

Lloyd, et al., "Activation of Somatostatin Receptor Subtype 2 Inhibits Acid Secretion in Rats," American Journal of Physiology: Gastrointestinal and Liver Physiology, American Physiological Society, vol. 268, No. 1, Pt. 1, 1995, pp. G102-G106.

Murphy, et al., "Octapeptide Analogs of Somatostatin Exhibiting Greatly Enhanced in Vito and in Vitro Inhibition of Growth Hormone Secretion in the Rat," Biochemical and Biophysical Research Communications, Academic Press, San Diego, CA, vol. 132, No. 3, Nov. 15, 1985.

* cited by examiner

*Primary Examiner* — Cecilia Tsang
*Assistant Examiner* — Thomas S Heard
(74) *Attorney, Agent, or Firm* — Gilberto M. Villacorta; Jeffrey R. Lomprey; Foley & Lardner LLP.

(57) ABSTRACT

SRIF peptide antagonists, which are selective for SSTR2 in contrast to the other cloned SRIF receptors and which bind with high affinity to the cloned human receptor SSTR2 but do not activate the receptor, have many useful functions. Because they do not bind with significant affinity to SSTR1, SSTR3, SSTR4 or SSTR5, their administration avoids potential undesirable side effects. Because they block the receptor function, they can be used therapeutically to block certain physiological effects which SSTR2 mediates. By incorporating radioiodine or the like in these SSTR2-selective SRIF antagonists, a labeled compound useful in drug-screening methods is provided. Alternatively, for use in therapy, highly radioactive moieties can be N-terminally coupled, complexed or chelated thereto.

15 Claims, No Drawings

US 7,960,342 B2

RECEPTOR(SSTR2)-SELECTIVE SOMATOSTATIN ANTAGONISTS

This application claims priority from U.S. Provisional Patent Application Ser. No. 60/829,637 filed Oct. 16, 2006, the disclosure of which is incorporated herein by reference.

This invention was made with Government support under Grant No. DK-59953 awarded by the National Institutes of Health. The Government has certain rights in this invention.

This invention is directed to peptides related to somatostatin and to methods for pharmaceutical treatment of mammals using such peptides. More specifically, the invention relates to shortened receptor-selective somatostatin peptide antagonists and the inclusion of amino acid substitutions and/or additions in such peptides that confer receptor-selectivity thereto, to pharmaceutical compositions containing such peptides, to such peptides complexed with or conjugated to radioactive nuclides, to methods of diagnostic and therapeutic treatment of neoplastic and non-neoplastic mammalian diseases using such peptides, particularly peptides that are coupled to chelators or otherwise labeled, and also to methods for screening for more effective drugs using such peptides.

BACKGROUND OF THE INVENTION

The cyclic tetradecapeptide somatostatin-14 (SRIF) was originally isolated from the hypothalamus and characterized as a physiological inhibitor of growth hormone (GH) release from the anterior pituitary. It was characterized by Guillemin et al. and was described in U.S. Pat. No. 3,904,594. This tetradecapeptide has a bridging or cyclizing bond between the sulfhydryl groups of the two cysteinyl amino acid residues in the 3- and 14-positions. SRIF affects multiple cellular processes and is also known to inhibit the growth of certain tumors. The analog [D-Trp$^8$]-SRIF, having the amino acid sequence: (cyclo 3-14)H-Ala-Gly-Cys-Lys-Asn-Phe-Phe-D-Trp-Lys-Thr-Phe-Thr-Ser-Cys-OH, was disclosed in U.S. Pat. No. 4,372,884 and stated to have many times greater potency to inhibit release of GH than SRIF.

SRIF induces its biological effects by interacting with a family of membrane-bound structurally similar receptors. Five SRIF receptors have been cloned and are referred to as SSTR1-5. All five receptors bind SRIF and SRIF-28 with high affinity. Selective agonists at SSTR2 and SSTR5 have been identified and used to reveal distinct functions of these receptors. These two receptors are believed to be the predominant subtypes in peripheral tissues. SSTR2 is believed to mediate the inhibition of growth hormone, glucagon and gastric acid secretion. U.S. Pat. No. 5,846,934 describes analogs which are stated to have some specificity for SSTR2. Octreotide, an agonist, shows some specificity for SSTR2 (see Yang et al., 1998, PNAS USA 95: 10836). In contrast, SSTR5 appears to be primarily involved in the control of insulin and amylase release. International Publication No. WO 97/11962 described analogs which are stated to have some specificity for SSTR5. SSTR3 mediates inhibition of gastric smooth muscle contraction. U.S. Pat. No. 6,579,967 discloses somatostatin analogs which are specific to SSTR3, the disclosure of which is incorporated herein by reference. SSTR4 is found in the pituitary, lungs, GI tract, kidneys, and in certain tumors to the substantial exclusion of the other SRIF receptors; it is believed to be activated upon binding by SRIF. U.S. published Patent Application No. 2002/0137676 discloses methods for treatment of endothelial cells using somatostatin receptor-selective ligands which are specific either to SSTR1 or SSTR4. U.S. Pat. Nos. 5,750,499 and 7,019,109 disclose somatostatin peptide analogs which are selective for SSTR1, the disclosures of which are incorporated herein by reference. Published U.S. Patent Application No. 2005/0245438 discloses receptor-selective somatostatin peptide analogs which are specific to SSTR4. These overall findings indicate that different receptor subtypes mediate distinct functions of SRIF in the body.

Somatostatin receptors are expressed in pathological states, particularly in neuroendocrine tumors of the gastrointestinal tract. Most human tumors originating from the somatostatin target tissue have conserved their somatostatin receptors. It was first observed in growth hormone producing adenomas and TSH-producing adenomas; about one-half of endocrine inactive adenomas display somatostatin receptors. Ninety percent of the carcinoids and a majority of islet-cell carcinomas, including their metastasis, usually have a high density of somatostatin receptors. However, only 10 percent of colorectal carcinomas and none of the exocrine pancreatic carcinomas contain somatostatin receptors. The somatostatin receptors in tumors can be identified using in vitro binding methods or using in vivo imaging techniques; the latter allow the precise localization of the tumors and their metastasis in the patients. Because somatostatin receptors in gastroenteropancreatic tumors are functional, their identification can be used to assess the therapeutic efficacy of an analog to inhibit excessive hormone release in the patients.

Somatostatin peptide antagonists that bind strongly to SSTR2, while at the same time showing only minimal propensity for binding to the other 4 receptors, would be valuable to have. Thus, the search has continued for such somatostatin peptide antagonists which are highly selective for SSTR2 but are not internalized into cells.

SUMMARY OF THE INVENTION

Certain modifications have now been discovered which are effective to create peptide analogs of SRIF that are selective for SSTR2 in contrast to the other cloned SRIF receptors. A class of somatostatin peptide analogs has been discovered which are highly SSTR2 selective, which are antagonists of somatostatin, and which, although not internalized in cells having SSTR2 receptors, are taken up in quantities that are surprisingly greater than are comparable receptor-selective somatostatin peptide agonists. The resultant peptides bind selectively to cloned SSTR2 without activating the receptor, and these peptide analogs, when iodinated or otherwise radiolabeled, will retain their desirable biological properties. Thus, these novel peptides are useful in determining the tissue location and cellular expression of the receptor SSTR2, as well as in regulating certain pharmacological functions without certain accompanying side effects heretofore characteristic of administering SRIF. These SRIF peptide antagonists, when radiolabeled, can be used in scintigraphy in order to locate, i.e. localize, tumors expressing these receptors, either in vitro or in vivo, using SPECT or PET; other labels as well known in this art, e.g. fluorescent labels, can alternatively be used. When they include an appropriate chelated radionuclide as known in this art, these analogs can serve as radiopharmaceuticals which are suitable for radionuclide therapy in treatment of such tumors.

The SRIF peptide antagonists of the invention inhibit the binding of $^{125}$I-[Tyr$^{11}$]SRIF and $^{125}$I-[Leu$^8$,D-Trp$^{22}$,Tyr$^{25}$]SRIF-28 to the cloned human receptor SSTR2, but they do not strongly bind to SSTR1, SSTR3, SSTR4 or SSTR5. Thus, unlabeled antagonists might be administered to therapeutically block the functioning of this receptor. These SRIF antagonists, to which $^{99m}$Tc, $^{111}$In, $^{68}$Ga or $^{90}$Y, for example, has been coupled by a chelator, such as DOTA or DTPA (or to which another complexing/conjugating agent is linked to the N-terminus for the purpose of attaching a moiety useful for diagnostic or therapeutic purposes), do not significantly bind to SSTR1, 3, 4 or 5 but continue to bind potently and saturably to SSTR2.

Preferred SRIF antagonists not only bind selectively to SSTR2, but they bind thereto with high affinity. By selective binding is meant that they exhibit a $K_D$ or an $IC_{50}$ with SSTR2 which is about one-hundredth or less of that with respect to all 4 other receptors. Preferred analogs will be at least about 200 times more selective for SSTR2 than for any other SRIF receptor, and more preferably at least about 500 times more selective.

These SRIF analogs can also be readily labeled and thus effectively used in drug screening, imaging, diagnosis and radionuclide therapy. For example, these analogs carrying detectable labels are useful in localizing such receptors in the body and in diagnosing the locations of tumors, particularly neuroendocrine tumors. As radionuclide therapeutic agents, they are considered to be particularly useful in combating tumors expressing the SSTR2 receptors; moreover, they are able to accomplish this without the side effects, i.e. without destroying a substantial part of neighboring tissue as a result of interacting with a plurality of SRIF receptors.

In one particular aspect, the invention provides a cyclic somatostatin (SRIF) peptide antagonist which selectively binds the SRIF receptor SSTR2 without triggering internalization into a cell, which peptide comprises the amino acid sequence (cyclo3-14)$Xaa_1$-$Xaa_2$-D-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$ wherein $Xaa_1$ is des-Xaa; $Xaa_2$ is Trp(A), Phe(B), Nal or Tyr, where A is H, Cl, F, Br, Me, $NO_2$, OMe or N-formyl and B is H, halogen, $CH_3$, $NO_2$ or $OCH_3$; D-$Xaa_3$ is D-Cys, D-Pen, D-HCys or another D-isomer α-amino acid having an SH-side chain; $Xaa_4$, $Xaa_5$ and $Xaa_6$ are des-Xaa; $Xaa_7$ is Aph ($Q_1$), Tyr(X), Ala(thienyl) or Trp(A) where $Q_1$ is Cbm, OH-Cbm, $CH_3$-Cbm, $OCH_3$-Cbm, OEt-Cbm, Cbm-Et(OEt)$_2$ or Hor and X is H or halogen; $Xaa_8$ is D-Trp(A), Trp(A), Tyr, D-Tyr, Phe(B), D-Phe(B), L or D-BzlHis, L or D-(DNP)His, L or D-Aph(Cbm); $Xaa_9$ is Lys, $N^\alpha$MeLys, hLys, $N^\alpha$MehLys, Orn or $N^\alpha$MeOrn; $Xaa_{10}$ is Thr, Ser or Val; $Xaa_{11}$, $Xaa_{12}$ and $Xaa_{13}$ are des-Xaa; $Xaa_{14}$ is Cys, Pen, hCys or another L-isomer α-amino acid having an SH side chain; and $Xaa_{15}$ is 2Nal, D-2Nal, Aph($Q_2$), D-Aph($Q_2$), ($R_1$)Cha, ($R_1$)D-Cha, ($R_1$)Leu, ($R_1$)D-Leu, Tyr, D-Tyr, Trp, D-Trp or des-Xaa; where $R_1$ is H or $C^\alpha$Me, and $Q_2$ is Cbm, OH-Cbm, $CH_3$-Cbm, $OCH_3$-Cbm or OEt-Cbm. A chelator-containing moiety may be coupled at the N-terminus as known in the art. Alternatively, a chelator-containing moiety may be complexed (for example biotin-avidin system) to its complement at the N-terminus of the peptide.

In a more particular aspect, the invention provides a cyclic somatostatin (SRIF) analog peptide which selectively binds the SRIF receptor SSTR2, which peptide comprises the amino acid sequence cyclo(3-14)$Xaa_1$-$Xaa_2$-D-Cys-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-Cys-$Xaa_{15}$-$NH_2$ wherein $Xaa_1$ is des-Xaa; $Xaa_2$ is chloro or nitro Phe; $Xaa_4$, $Xaa_5$ and $Xaa_6$ are des-Xaa; $Xaa_7$ is Aph (Hor), Tyr or ITyr; $Xaa_8$ is D-Aph(Cbm) or D-Trp; $Xaa_9$ is Lys, Orn, hLys, $N^\alpha$MeLys or $N^\alpha$MeOrn; $Xaa_{10}$ is Thr; $Xaa_{11}$, $Xaa_{12}$ and $Xaa_{13}$ are des-Xaa; and $Xaa_{15}$ is 2Nal or D-Tyr.

In a further particular aspect, the invention provides a method of externally imaging tissue in the body of a human being, which expresses SSTR2, comprising: (i) administering to a human being, in a quantity sufficient for external imaging, a composition comprising a SRIF peptide antagonist that is selective for SSTR2 in contrast to the other cloned SRIF receptors and which binds with high affinity to the cloned human receptor SSTR2 but does not activate the receptor, said SRIF peptide antagonist bearing a detectable label, and (ii) subjecting the human being to external imaging.

In a still further particular aspect, the invention provides a method of irradiating neoplastic tissue in the body of a human being, which expresses SSTR2, comprising: (i) administering to a human being, in a quantity sufficient for irradiating neoplastic tissue, a composition comprising a SRIF peptide antagonist that is selective for SSTR2 in contrast to the other cloned SRIF receptors and which binds with high affinity to the cloned human receptor SSTR2 but does not activate the receptor, said SRIF peptide antagonist bearing a radioactive label, and (ii) allowing the SRIF peptide antagonist to bind to the neoplastic tissue.

In another particular aspect, the invention provides a method of detecting, in the body of a human being, tumors and their metastases having SSTR2 in tissues, which do not contain substantial quantities of SSTR2 when in healthy condition or in non-neoplastic conditions of chronic inflammation, which method comprises (i) administering to said human, in a quantity sufficient for external imaging, a composition comprising a peptide according to claim 1, said peptide being labeled with (a) a radioactive metal isotope which is linked through a suitable chelator or (b) a paramagnetic metal atom or labeled with a radioactive halogen isotope, and thereafter (ii) subjecting said human to external imaging, by radioactive scanning or by magnetic resonance imaging, to determine the targeted sites in the body thereof in relation to the background activity, in order to allow detection and localization of said tumors in the body semiquantitatively.

The present invention further provides a method of screening for ligands that are highly selective for SSTR2 using a pharmacophore model that is premised upon a pattern of ligand features that are determined to be required for selective binding. Such method may comprise carrying out a competitive binding assay with an SSTR2 receptor, a ligand according to the present invention, and a candidate antagonist, wherein said ligand has a suitable detectable label; determining the ability of the candidate antagonist to displace the labeled ligand; and testing said candidate antagonist for its ability to antagonize an activity associated with SRIF.

DETAILED DESCRIPTION OF THE PREFERRED EMBODIMENTS

The standard 3-letter abbreviations identify the alpha-amino acid residues, and where the amino acid residue has isomeric forms, it is the L-form of the amino acid that is represented unless otherwise expressly indicated, e.g. Ser=L-serine. By L or D is meant either of the D- and L-isomers of a particular α-amino acid. When reference is hereinafter made to a position in the peptide, such is meant to refer to the corresponding position of the native 14-residue somatostatin (SRIF) peptide.

SRIF peptide antagonists are provided having a selective affinity for the SRIF receptor SSTR2; they preferably also have a high affinity for SSTR2, i.e. equal to a $K_D$ of about 10 nanomolars or less. These peptides encompass shortened cyclic analogs of SRIF, where the ring portion is shortened to only 6 residues, and where there is one residue at the N-terminus and preferably a residue is also added at the C-terminus. In other words, the 1-, 4-, 5-, 6-, 11-, 12- and 13-position residues are deleted from the 14-residue native SRIF, creating heptapeptides, and preferably a residue (i.e. residue 15) is also added at the C-terminus, which creates an octapeptide.

Examples of representative peptide antagonists exhibiting the desired specificity for SSTR2 are provided by the following amino acid sequence, which is based upon a numbering system consistent with the 14-residue sequence of native mammalian SRIF, wherein the residues at positions 1, 4-6 and 11-13 are preferably eliminated: (cyclo3-14)$Xaa_1$-$Xaa_2$-D-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$ wherein $Xaa_1$ is des-Xaa; $Xaa_2$ is Trp(A), Phe(B), Nal or Tyr, where A is H, Cl, F, Br, Me, $NO_2$, OMe or N-formyl and B is H, halogen, $CH_3$, $NO_2$ or $OCH_3$; D-$Xaa_3$ is D-Cys, D-Pen, D-HCys or another D-isomer α-amino acid having an SH-side chain; $Xaa_4$, $Xaa_5$ and $Xaa_6$ are des-Xaa; $Xaa_7$ is Aph($Q_1$), Ala(thienyl), Tyr(X) or Trp(A) where $Q_1$ is Cbm, OH-Cbm, $CH_3$-Cbm, $OCH_3$-Cbm, OEt-Cbm, Cbm-Et$(OEt)_2$ or Hor and X is H or halogen; $Xaa_8$ is D-Trp(A), Trp(A), Tyr, D-Tyr, Phe(B), D-Phe(B), L or D-Bzl-His, L or D-(DNP)His, L or D-Aph(Cbm); $Xaa_9$ is Lys, $N^\alpha$MeLys, hLys, $N^\alpha$MehLys, Orn or $N^\alpha$MeOrn; $Xaa_{10}$ is Thr, Ser or Val; $Xaa_{11}$, $Xaa_{12}$ and $Xaa_{13}$ are des-Xaa; $Xaa_{14}$ is Cys, Pen, hCys or another L-isomer α-amino acid having an SH side chain; and $Xaa_{15}$ is 2Nal, D-2Nal, Aph($Q_2$), D-Aph($Q_2$), ($R_1$)Cha, ($R_1$)D-Cha, ($R_1$)Leu, ($R_1$)D-Leu, Tyr, D-Tyr, Trp, D-Trp or des-Xaa; where $R_1$ is H or $C^\alpha$Me, and $Q_2$ is Cbm, OH-Cbm, $CH_3$-Cbm, $OCH_3$-Cbm or OEt-Cbm. Tyr in the 2-position may be radioiodinated, or a complexing, conjugating or chelating agent can be attached directly or via a linker to the α-amino group of the N-terminal residue of any of these peptide analogs which is capable of linking a radioactive nuclide thereto. For example, a macrocyclic chelator, such as DOTA, can be added at the N-terminus either by joining it directly to $Xaa_2$ or indirectly thereto using a linker such as $GABA$ (gamma amino butyric acid, see e.g. U.S. Pat. No. 6,022,523) or βAla.

One preferred subgenus of SRIF analogs comprises the amino acid sequence: (cyclo 3-14)$Xaa_1$-$Xaa_2$-D-$Xaa_3$-$Xaa_4$-$Xaa_5$-$Xaa_6$-$Xaa_7$-$Xaa_8$-Lys-Thr-$Xaa_{11}$-$Xaa_{12}$-$Xaa_{13}$-Cys wherein $Xaa_2$ is substituted Phe; D-$Xaa_3$ is D-Cys; $Xaa_7$ is Aph($Q_1$), Tyr or ITyr; and $Xaa_8$ is D-Trp or D-Aph(Cbm). It should be understood that the remaining Xaa groups are as defined hereinbefore whenever they are not specified.

Generally for purposes of this application, reference to Trp and D-Trp in the description other than in a specific example should be understood to include the unsubstituted residue as well as a residue where a single substitution for hydrogen is made in either the 5- or 6-position on Trp, and with such substituents being selected from chloro, fluoro, bromo, methyl, nitro and methoxy, with chloro, fluoro and bromo being preferred or with formyl substituting the hydrogen of the indole N. By Nal is mean the isomer of alanine which is substituted by naphthyl on the β-carbon atom, with the attachment to naphthalene preferably being to the 2-position on the ring, or optionally to the 1-position. By Aph is meant aminophenylalanine, where the amino group is preferably attached to the 4-position on the phenyl ring, but attachment at either the 2- or 3-position is generally equivalent. By Aph (Cbm) is meant 4-ureido-phenylalanine. By Aph(OH-Cbm) is meant 4-(3-hydroxy)-ureido-phenylalanine. By Aph ($CH_3$-Cbm) is meant 4-(3-methyl)-ureido-phenylalanine. By Aph ($OCH_3$-Cbm) is meant 4-(3-methoxy)-ureido-phenylalanine. By Aph[(EtO)$_2$Et-Cbm] is meant 4-{3-[2-(2-ethoxy-ethoxy)-ethyl]}-ureido-phenylalanine. By ITyr is meant iodinated L-tyrosine, e.g. 3-iodo-Tyr. By Cpa is meant chloro-Phe, and preferably 4ClPhe. By Aph(Hor) is meant 4-[(2,6-dioxo-hexahydro-pyrimidine-4-carbonyl)-amino]-phenylalanine. By SRIF is meant the 14-residue cyclic peptide somatostatin. By Cha is meant cyclohexylalanine, and by Pen is meant penicillamine (β-mercapto valine). By hLys or hCys is meant the α-amino acid with one additional $CH_2$ group in the side chain.

The C-terminus is usually amidated, although an equivalent, e.g. Gly-OH, might be used. The N-terminus may be modified in various ways without significantly adversely affecting the binding affinity, all of which modifications in these cyclic peptides are considered to be included as a part of the peptides of the overall invention. For example, a variety of additions may be made, and preferably are made, to the N-terminal amino acid in the form of a complexing or conjugating agent (Z) which can then be used to join a desired moiety to the peptide or to provide labeling. Generally such a moiety Z may be selected from the group consisting of DOTA- and DTPA-based chelators, NOTA-based chelators, carbonyl compounds, 2-hydrazino nicotinamide (HYNIC), $N_4$-chelators, desferrioxamin, $N_xS_y$-chelators, all optionally complexed with a radioisotope, Tyrosine (Tyr) for halogenation, a fluorescent dye and biotin. Cpa may also serve as a precursor for tritiation. For example, a chelator, such as DTPA, DOTA, HYNIC and $P_2S_2$—COOH may be attached; preferred chelators may include p-$NH_2$-Bz-DOTA (2-p-aminobenzyl-1,4,7,10-tetraazacyclododecane-1,4,7,10-tetraacetic acid), and DOTA-p-$NH_2$-anilide [1,4,7,10-tetraazacyclododecane-1,4,7,10-tetraacetic acid mono(p-aminoanilide)]. Alternatively, a chelating agent may be covalently linked to the N-terminus via a suitable linker (L) if desired; suitable linkers L include tyrosine, lysine, diaminobutyric acid, diaminopropionic acid, polyethylene glycol, fatty acids and their derivatives, β-alanine, 5-amino valeric acid, sarcosine, and gluceronic acid. When Tyr appears at the N-terminus, it may be radioiodinated or otherwise labeled. Acyl groups having not more than about 20 amino acids may also be present at the N-terminus, as the N-terminal residue may also be acylated, if desired, with a bulky moiety without loss of selectivity.

Selectivity for binding of the analog peptides of the invention to SSTR2 has been demonstrated by testing their interaction with the five different cloned human SRIF receptors as described in great detail hereinafter. Generally, recombinant cells expressing the receptor are washed and homogenized to prepare a crude protein homogenate in a suitable buffer, as known in the art. In a typical assay, an amount of protein from the cell homogenate is placed into a small volume of an appropriate assay buffer at an appropriate pH. Candidate substances, such as potential SRIF agonists and antagonists, are added to the admixture in convenient concentrations, and the interaction between the candidate substance and the receptor polypeptide is monitored. The peptides of the invention bind substantially strongly only to SSTR2, and their binding exhibits high affinity.

Receptor binding assays are performed on cloned SRIF receptors, and competitive assays are used to generate $IC_{50}$ values which are indicative of the concentration of a competitive ligand necessary to displace a saturation concentration of a target ligand being measured from 50% of binding sites.

According to one aspect of the present invention, a method of intraoperatively detecting malignant tumors in the body of a human being in tissues which in healthy condition do not contain substantial quantities of SSTR2 comprises (i) administering to such being a composition comprising, in a quantity sufficient for detection by a gamma detecting probe, an SSTR2-selective peptide, which peptide is labeled, e.g. radioactively with $^{99m}Tc$, $^{161}Tb$, $^{90}Y$, $^{177}Lu$, $^{123}I$ or $^{125}I$ and (ii) after allowing the active substance to be bound and taken up in said tumors and after blood clearance of radioactivity, subjecting such being to a radiodetection technique in the relevant area of the body by using a gamma-detecting probe.

The SRIF antagonists of the present invention are highly selective for SSTR2, and they are taken up in greater quantities than earlier SRIF peptide agonists that were only partially specific to SSTR2. More importantly, SRIF antagonists are considered to be useful in combating cancers which express SSTR2 using radiotherapy where the success of which is directly dependent upon the amount of radiation taken up by a tumor; thus, they are expected to be more effective than known agonists for radiotherapy of tumors. Of course, they are also considered to be particularly useful in scintigraphy to determine the distribution of cells and tissues expressing SSTR2 throughout the body, and the use of external imaging by radioactive scanning or by magnetic resonance allows semiquantitative detection within the body. They are further useful in selectively blocking certain of the pharmacological effects that are mediated by SSTR2, the many effects of SRIF having been determined over the past 2 decades.

More specifically, these radioactive antagonists are considered to be particularly useful for the therapeutic treatment of malignant tumors in the body of a human being in tissues which in healthy condition do not contain substantial quantities of SSTR2. Such SSTR2-selective peptide antagonist is administered a composition which includes a quantity effective for scintigraphy or for combating or controlling tumors, and it may be labeled with an isotope selected from the group consisting of $^{186}$Re, $^{188}$Re, $^{111}$In, $^{113m}$In, $^{71}$As, $^{10}$Y, $^{64}$Cu, $^{67}$Cu, $^{99m}$Tc, $^{169}$Er, $^{121}$Sn, $^{127}$Te, $^{142}$Pr, $^{143}$Pr, $^{66}$Ga, $^{67}$Ga, $^{68}$Ga, $^{72}$Ga, $^{127}$Te, $^{195}$Pt, $^{211}$At, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{111}$Ag, $^{124}$I and $^{131}$I.

Labeled SRIF analogs of the invention are also considered to be useful in drug-screening assays to screen for new effective peptide and non-peptide agents which will bind with high affinity to SSTR2 and which may be highly effective antagonists. Using a ligand of the invention that is selective for the receptor SSTR2, one can obtain a baseline activity for the recombinantly produced receptor. A competitive binding assay with the SSTR2, the labeled ligand and the candidate may then be carried out to determine its relative binding affinity. Alternatively, prospective candidates for inhibitors or modifiers, i.e. antagonists, of the receptor function, can be directly incorporated into a test mixture to test the effect of such candidate on the receptor. By comparing the extent of receptor activity in the presence or absence of the candidate substance, one can then obtain information regarding the effect of the candidate substance on the normal function of the receptor and thus determine its function as either an agonist or an antagonist compared to a known SSTR2-selective analog. The cyclic SRIF peptides described in the following Examples are antagonists, and they can be employed to mediate the normal function of SSTR2.

The peptides of the present invention can be synthesized by classical solution synthesis, but the amidated peptides are preferably synthesized by solid-phase technique, as on a methylbenzhydrylamine (MBHA) resin or a BHA resin, as is well-known in this art. Peptides having a free carboxyl C-terminus are preferably synthesized as taught in U.S. Pat. No. 7,019,109. Peptides having a amidated C-terminus may be synthesized as taught in U.S. Pat. No. 5,874,227. Solid-phase synthesis is conducted in a manner to stepwise add amino acids in the chain beginning at the C-terminus in the manner set forth in either of those U.S. patents, the disclosures of which are incorporated herein by reference. Side-chain protecting groups, which are well known in the art, are preferably included as a part of any amino acid which has a particularly reactive side chain, and optionally may be used in the case of others such as Trp, when such amino acids are coupled onto the chain being built upon the resin. Such synthesis provides a fully protected intermediate peptidoresin. Generally, protecting groups are split off and the peptide is cleaved from the resin support before oxidizing to create a disulfide bond between the Cys side chains.

The SRIF analogs of the invention are generally effective at levels of less than 100 micrograms per kilogram of body weight. For prolonged action, it may be desirable to use dosage levels of about 0.1 to about 2.5 milligrams per kilogram of body weight. These analogs are soluble in water and thus can be prepared as relatively concentrated solutions for administration.

The following Examples illustrate the provision of a number of SRIF peptide antagonists embodying various features of the invention. In each peptide, the cysteine residues in positions 3 and 14 are joined by the cyclizing disulfide bond.

EXAMPLE 1

The somatostatin analog DOTA-des-AA$^{1,4,5,6,11,12,13}$[Cpa$^2$, D-Cys$^3$, Tyr$^7$, D-4Aph(Cbm)$^8$]-SRIF-2Nal-NH$_2$ having the structure:

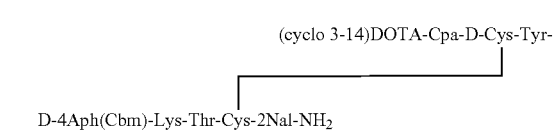

is synthesized. Solid phase methodology employing the BOC strategy is used to synthesize the octapeptide in a stepwise manner on an MBHA resin, generally as described in Example II of the '277 patent. Boc-D-4Aph(Cbm)-OH was pre-made as described in an earlier publication by Jiang and coupled at position 8.

After cleaving the peptide from the resin and simultaneously removing side chain protecting groups (except Fmoc from Lys) by HF, the peptide was oxidized to create the disulfide bridge in 75% acetic acid solution by adding a 10 percent solution of iodine in methanol until the resultant solution remained orange colored, then stirring for 40 minutes and quenching with ascorbic acid. The crude peptide was purified by preparative RP-HPLC, using a linear gradient 1% B per 1 min increases from the baseline % B (Eluent A=0.1% TFA, eluent B=60% CH$_3$CN, 40% A) at a flow rate of 100 ml/min. DOTA was then coupled at the N-terminus as a chelator by adding DOTA-NHS.3TFA.HPF$_6$ (Macrocyclics, Dallas, Tex.) (198 mg, ~20 µM) in DMF (1 ml) and N,N'-diisopropylethylamine (DIPEA) (36 µl, ~22 µM) to the purified peptide (32 mg, ~20 µM) in dry N,N-dimethylformamide (DMF, 3.5 ml). The mixture was stirred at room temperature overnight. The progress of the reaction was followed by analytical HPLC, and MS analysis showed the desired product, pure DOTA-des-AA$^{1,4,5,6,11,12,13}$[Cpa$^2$, D-Cys$^3$, Tyr$^7$, D-4Aph (Cbm)$^8$, Lys (Fmoc)$^9$]-SRIF-2Nal-NH$_2$, had been obtained. After completion of the reaction, removal of the Fmoc protecting group from the Lys$^9$ side chain was achieved by adding 4 ml of a solution of 20% piperidine in DMF and waiting 30 minutes. DOTA-des-AA$^{1,4,5,6,11,12,13}$[Cpa$^2$, D-Cys$^3$, Tyr$^7$, D-4Aph (Cbm)$^8$]-SRIF-2Nal-NH$_2$ was desalted by preparative RP-HPLC using the same conditions as described above. The purity of the final cyclic DOTA-peptide-conjugate was determined by analytical CZE. It was 94% pure.

MS analysis shows an [M+H]+ mass of 1583.72 Da which compares very favorably to the calculated mass of 1583.62 Da. The peptide is hereinafter referred to as Peptide No. 1.

EXAMPLE 2

The initial synthesis described in Example 1 is repeated with two changes; 4Aph (Cbm) and D-Trp are used in the 7- and 8-positions to provide the octapeptide-resin: des-AA$^{1,4,5,6,11,12,13}$[Cpa$^2$, D-Cys$^3$, 4Aph(Cbm)$^7$, D-Trp$^8$, Lys (Fmoc)$^9$]-SRIF-2Nal-MBHA resin.

After cleaving the peptide from the resin as the amide and simultaneously removing the protecting groups from the side chains of the amino acids (except Fmoc from Lys) by HF, the peptide was oxidized to create the disulfide bridge in 75% acetic acid solution by adding a 10 percent solution of iodine in methanol until the resultant solution remains orange colored, then stirring for 40 minutes and quenching with ascorbic acid. The crude peptide was purified by preparative RP-HPLC, using a linear gradient 1% B per 1 min increases from the baseline % B (Eluent A=0.1% TFA, eluent B=60% CH$_3$CN, 40% A) at a flow rate of 100 ml/min. To the purified peptide (34 mg~24 µM) in dry N,N-dimethylformamide (DMF, 3.5 ml) was added DOTA-NHS.3TFA.HPF$_6$ (Macrocyclics, Dallas, Tex.) (24 mg, 24.2 µM) in DMF (150 µl) and N,N'-diisopropylethylamine (DIPEA) (40 µl, 24 µM). The mixture was stirred at room temperature overnight. The progress of the reaction was followed by analytical HPLC, and after completion of the reaction, 1 ml of piperidine was added to the reaction mixture to remove the Fmoc protecting group from the Lys$^9$ side chain for 30 minutes resulting in DOTA-des-AA$^{1,4,5,6,11,12,13}$[Cpa$^2$, D-Cys$^3$, 4Aph(Cbm)$^7$, D-Trp$^8$]-SRIF-2Nal-NH$_2$, which has the formula:

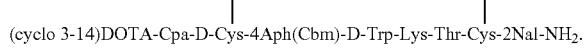

(cyclo 3-14)DOTA-Cpa-D-Cys-4Aph(Cbm)-D-Trp-Lys-Thr-Cys-2Nal-NH$_2$.

This peptide was desalted by preparative RP-HPLC using the same conditions as described above. The purity of the final cyclic DOTA-peptide-conjugate was determined by analytical CZE to be about 98% pure. MS analysis shows an [M+H]+ mass of 1606.50 Da, which compares favorably with the calculated value of 1606.64 Da. It is referred to as Peptide No. 2.

EXAMPLE 3

The synthesis set forth in Example 1 is repeated omitting 2Nal at the C-terminus and substituting 4Aph(Hor) for Tyr$^7$. Boc-4Aph(Hor)-OH was premade as described in an earlier publication by G. Jiang, J. Stalewski, et al., (2001). "GnRH antagonists: A new generation of long acting analogues incorporating urea functions at positions 5 and 6", *J. Med. Chem.* 44(3): 453-467. Cleavage, deprotection, cyclization and purification of the peptide are carried out as in Example 1. The purified cyclic peptide has the formula:

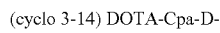

(cyclo 3-14) DOTA-Cpa-D-

-Cys-4Aph(Hor)-D-4Aph(Cbm)-Lys-Thr-Cys-NH$_2$.

It has a purity on CZE of about 98%. It is referred to as Peptide No. 3. MS analysis shows an [M+H]+ mass of 1525.68 Da, which compares favorably to the calculated value of 1525.58 Da.

EXAMPLE 4

The synthesis set forth in Example 1 is repeated with one change, instead of pCl-Phe at the N-terminus, pNO$_2$-Phe is used. Cleavage, deprotection, cyclization and purification of the peptide are carried out as in Example 1. The purified cyclic peptide has the formula:

(cyclo 3-14)DOTA-pNO$_2$-Phe-D-

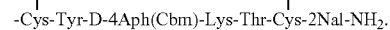

-Cys-Tyr-D-4Aph(Cbm)-Lys-Thr-Cys-2Nal-NH$_2$.

It has a purity on CZE of about 98%. It is referred to as Peptide No. 4. MS analysis shows an [M+H]+ mass of 1594.17 Da which compares favorably to the calculated value of 1594.65 Da.

EXAMPLE 5

The initial synthesis described in Example 1 is repeated with one change; Aph(Hor) is used instead of Tyr in the 7-position to provide the octapeptide-resin: des-AA$^{1,4,5,6,11,12,13}$[Cpa$^2$, D-Cys$^3$, 4Aph(Hor)$^7$, D-Aph(Cbm)$^8$, Lys (Fmoc)$^9$]-SRIF-2Nal-MBHA resin. Reactions are then carried out as described in Example 2 resulting in DOTA-des-AA$^{1,4,5,6,11,12,13}$[Cpa$^2$, D-Cys$^3$, 4Aph(Hor)$^7$, D-Aph (Cbm)$^8$]-SRIF-2Nal-NH$_2$, which has the formula:

(cyclo 3-14)DOTA-Cpa-D-Cys-

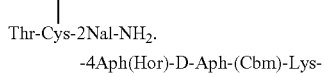

Thr-Cys-2Nal-NH$_2$.
-4Aph(Hor)-D-Aph-(Cbm)-Lys-

The purity of the final cyclic DOTA-peptide-conjugate was determined by analytical CZE to be about 98% pure. It is referred to as Peptide No. 5. MS analysis shows an [M+H]+ mass of 1722.56 Da which compares favorably to the calculated value of 1722.65 Da.

EXAMPLE 6

The synthesis set forth in Example 5 is repeated, substituting D-Tyr for 2Nal at the C-terminus. Cleavage, deprotection, cyclization and purification of the peptide are carried out as in Example 1. The purified cyclic peptide has the formula:

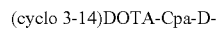

(cyclo 3-14)DOTA-Cpa-D-

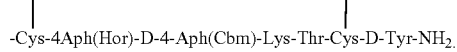

-Cys-4Aph(Hor)-D-4-Aph(Cbm)-Lys-Thr-Cys-D-Tyr-NH$_2$.

It has a purity on CZE of about 98%. It is referred to as Peptide No. 6. MS analysis shows an [M+H]+ mass of 1688.83 Da which compares favorably to the calculated value of 1688.64 Da.

EXAMPLE 7

The synthesis set forth in Example 4 is repeated substituting D-Tyr for 2Nal at the C-terminus. Cleavage, deprotection, cyclization and purification of the peptide are carried out as in Example 1. The purified cyclic peptide has the formula:

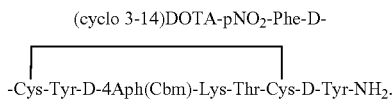
-Cys-Tyr-D-4Aph(Cbm)-Lys-Thr-Cys-D-Tyr-NH$_2$.

It has a purity on CZE of about 98%. It is referred to as Peptide No. 7. MS analysis shows an [M+H]$^+$ mass of 1560.63 Da which compares favorably to the calculated value of 1560.83 Da.

EXAMPLE 8

The synthesis described in Example 7 is repeated with two changes; ITyr is used at the 7-position and D-Trp is used in the 8-position to provide the octapeptide-resin: des-AA$^{1,4,5,6,11,12,13}$[pNO$_2$-Phe$^2$, D-Cys$^3$, ITyr$^7$, D-Trp$^8$, Lys(Fmoc)$^9$]-SRIF-D-Tyr-MBHA resin.

After cleaving the peptide from the resin as the amide and carrying out reactions as generally described in Example 2, the peptide is obtained having the formula:

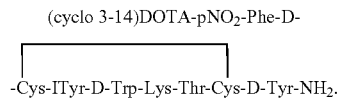
-Cys-ITyr-D-Trp-Lys-Thr-Cys-D-Tyr-NH$_2$.

The purity of the final cyclic DOTA-peptide-conjugate was determined by analytical CZE to be about 98% pure. It is referred to as Peptide No. 8. MS analysis shows an [M+H]$^+$ mass of 1667.74 Da which compares favorably to the calculated value of 1667.52 Da.

In vitro Bioassay: The effects of the various somatostatin analogs are tested in vitro for their ability to bind to isolated cloned receptors expressed on CHO-K1 cells and CCL39 cells. CHO-K1 cells are grown in Ham's F-12 medium, and CCL39 cells are grown in Dulbecco's modified Eagle's medium/Ham's F-12(1:1) mix, supplemented with 10% fetal bovine serum, 100 U/ml penicillin and 100 μg/ml streptomycin, in humidified air containing 5% CO$_2$ at 37° C.

The molecular cloning of the genes encoding multiple somatostatin receptor subtypes permits the individual expression of these receptors in mammalian cells and the characterization of their respective pharmacological profiles. Five such receptor subtypes, termed SSTR1 through SSTR5, have been cloned and are reported and described in Raynor et al., *Molecular Pharmacology*, 43, 838-844 (1993) and in Raynor et al., *Molecular Pharmacology*, 44, 385-392 (1993). These references describe binding assays that can be used to determine whether particular SRIF analogs bind selectively to one or more of the 5 receptor types and also whether they bind to such receptor types with high or low affinity. Because these receptor types have now generally been characterized with regard to their pharmacological profiles, knowledge of the results of such binding studies, along with knowledge of the unique patterns of distribution of these receptors in the body indicate that each receptor subtype may mediate distinct but overlapping physiological effects of SRIF. As a result, compounds which bind selectively to receptors SSTR2, for example, can be used to modulate a particular physiological function of SRIF without potentially having an undesired effect resulting from another physiological function of SRIF which is mediated by other SRIF receptors.

Cells are washed twice with and scraped into ice-cold 0.05 M Tris-HCl (pH 7.4), collected by centrifugation, and homogenized using a rotor/stator/system in the same buffer. After centrifugation at 120 g for 5 min at 4° C., the supernatant is collected and centrifuged again at 48,000 g for 30 min at 4° C. The resulting pellet is resuspended in ice-cold Tris buffer, transferred into a microfuge tube, and centrifuged at 20,000 g for 15 min at 4° C. After withdrawal of the supernatant, the membrane pellet is stored at −80° C.

Receptor autoradiography is performed on 20 μm thick cryostat sections of the membrane pellets, mounted on microscope slides, and then stored at −20° C. For each of the tested compounds, complete displacement experiments are performed with the universal somatostatin ligand radioligand $^{125}$I-[Leu$^8$,D-Trp$^{22}$,Tyr$^{25}$]-somatostatin 28 that binds with strong affinity to all five receptors. Increasing concentrations of the unlabeled peptide are used ranging from 0.1-1000 nM. Unlabeled somatostatin-28 is run in parallel using the same increasing concentrations, as a control. IC$_{50}$ values are calculated after quantification of the data using a computer-assisted image processing system as known in this art. At concentrations of 100 nM, Peptide No. 1 had minimal effects on the binding of the SRIF-28 radioligand to SSTR1, SSTR3, SSTR4 and SSTR5. In contrast, it selectively bound to SSTR2, displacing the binding of the radioligand to human SSTR2 with an IC$_{50}$ value of about 1.8 nM.

The potencies of certain SRIF analogs to inhibit radioligand binding of $^{125}$I-[Leu$^8$,D-Trp$^{22}$,Tyr$^{24}$]SRIF-28 to the various cloned human SRIF receptors are shown in the following table wherein the IC$_{50}$ values are given in nanomolar concentration. The numbers in parentheses indicate the number of times the particular binding test was carried out.

TABLE

| | IC$_{50}$ (nM) | | | | |
|---|---|---|---|---|---|
| Compound | hSSTR1 | hSSTR2 | hSSTR3 | hSSTR4 | hSSTR5 |
| Peptide No. 1 406-034-15 | >1,000 (2) | 1.8 ± 0.2 (3) | >1,000 (2) | >1,000 (2) | >1,000 (2) |
| Peptide No. 2 363-246-15 | >1,000 (3) | 9.4 ± 1.6 (3) | >1,000 (2) | 816 ± 114 (3) | >1,000 (3) |
| Peptide No. 3 363-300-15 | >1,000 (2) | 230; 219 (2) | >1,000 (2) | >1,000 (2) | >1,000 (2) |
| Peptide No. 4 406-032-20 | >1,000 (2) | 1.5 ± 0 (2) | >1,000 (2) | >1,000 (2) | >1,000 (2) |
| Peptide No. 5 363-298-15 | >1,000 (2) | 1.7 ± 0.3 (3) | >1,000 (2) | >1,000 (2) | >1,000 (2) |
| Peptide No. 6 406-094-15 | >1,000 (2) | 0.6 ± 0.05 (2) | >1,000 (2) | >1,000 (2) | >1,000 (2) |
| Peptide No. 7 406-092-15 | >1,000 (2) | 0.53 ± 0.06 (2) | >1,000 (2) | >1,000 (2) | >1,000 (2) |
| Peptide No. 8 406-090-15 | >1,000 (2) | 1.02 ± 0.88 (2) | >1,000 (2) | 493 ± 206 (2) | >1,000 (2) |

Moreover, all the peptides tested and reported in the Table above showed no significant internalization in the cells while antagonizing octreotide-induced internalization. Peptides Nos. 1 and 4 to 8 exhibited very good binding properties and excellent tumor targeting properties in vivo, namely huge uptake in the sst2 tumors at 4 h and 24 h, and excellent tumor to kidney ratio; thus tumor uptake can be blocked by excess cold peptide.

The peptides of the invention not only provide more selective ligands for binding SSTR2, but the use of labeled peptides, for example, a radiolabeled version of Peptide No. 1, facilitates drug screening for even more effective antagonists. Screening assays, as are well known in the art which employ the receptor polypeptide SSTR2 directly from the recombinant host, can be used to identify agents useful in blocking or mimicking certain aspects of somatostatin as desired while eliminating the undesirable aspects of the hormone which may arise from activation or blocking of other receptors. In this respect, if a radioiodinated analog is desired for screening purposes, Tyr can be added at the N-terminus instead of DOTA, or Tyr can be used in the 2-position instead of Cpa, or a suitable radioligand can be attached by a DOTA chelator. Competitive binding assays with candidate compounds might first be carried out in this manner with SSTR2 to search for high binding affinity; then by screening the multiple SRIF receptors, it could be confirmed whether there was selective binding to only this receptor, as is desired. Non-radiolabeled peptides of the invention may be used to treat diseases of all organs known to express SSTR2, including the lung, gastrointestinal tract and kidneys.

Because, as shown above, additions to the N-terminus of the SRIF analog do not appear to adversely affect the selective binding, it should be clear that these compounds can be complexed with a radioactive nuclide for the purpose of carrying that agent to a tumor or other tissue for which apoptosis is desired. For example, suitable chelating agents, such as DOTA or DTPA or others, can be used to complex the SRIF analog with a highly radioactive metal as indicated hereinbefore. Some examples of suitable chelating groups for chelating a radioactive metal atom are tetradentate chelating agents or groups derived from ethylene diamine tetra-acetic acid (EDTA), diethylene triamine penta-acetic acid (DTPA), cyclohexyl 1,2-diamine tetra-acetic acid (CDTA), ethyleneglycol-0,0'-bis (2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetra-acetic acid (DOTA), hydroxyethyldiamine triacetic acid (HEDTA), 1,4,8,11-tetraazacyclo-tetradecane-N, N',N'',N'''-tetra-acetic acid (TETA), substituted DTPA, substituted EDTA. Other chelators, as well as radioactive agents, are disclosed in WO 95/22341 and WO 04/082722 and in U.S. Patent Publications 2004/0242842 and 2005/0070470, the disclosures of which are incorporated herein by reference. Preferred chelators are derived from EDTA and DOTA. Some suitable salts are $^{111}$In-oxinate and $^{99m}$Tc-tartrate, which can generally be formed in a simple manner under conditions that are not detrimental to the peptide antagonist, and $^{99m}$Tc(CO)$_3$ can be coupled via Tyr or a suitable tridendete chelator.

If desired, the solubility of the SRIF antagonists can be improved by acylation of the N-terminal amino group using a hydrophilic compound, such as hydroorotic acid (Hor) or the like, or by reaction with a suitable isocyanate, such as methylisocyanate or isopropylisocyanate, to create a urea moiety at the N-terminus. Other agents can also be N-terminally linked that will increase the duration of action of the SRIF antagonist as known in this art.

These SRIF antagonists or nontoxic salts thereof, combined with a pharmaceutically or veterinarily acceptable carrier to form a pharmaceutical composition, may be administered to animals, including humans and other mammals, either intravenously, subcutaneously, intramuscularly, percutaneously, e.g. intranasally, intracerebrospinally or orally. Such a pharmaceutical composition designed to be used for detecting malignant human tumors, including the metastasis thereof, in tissues may include, in addition to a pharmaceutically acceptable carrier material, and an optional pharmaceutically acceptable adjuvant, the labeled peptide antagonist as the active substance, in a quantity sufficient for external imaging, for detection by a gamma-detecting probe or for combating or controlling tumors. The peptide antagonists should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans should be under the direction of a physician to combat specific tumors and cancers or to mediate other conditions where the SSTR2 receptors exert a control function, such as coupling to a tyrosine phosphatase so that stimulation of this enzyme can be carried out to mediate the anti-proliferative effects of SRIF. The required dosage will vary with the particular condition being treated, with the severity of the condition and with the duration of desired treatment.

It has recently been determined that tumors often express several types of peptide receptors (Reubi, J. C.; Waser, B. *Concomitant expression of several peptide receptors in neuroendocrine tumours*: molecular basis for in vivo multireceptor tumour targeting. *Eur. J. Nucl. Med. Molec. Imaging* 2003, 30, 781-793.). Such groups of multiple peptide receptors may include sst2 receptors, as well as bombesin receptors, CCK receptors, VIP receptors, GLP-1 receptors, neurotensin receptors, secretin receptors, neuromedin B receptors and CRF receptors, etc. In such an instance, the administration of SSTR2 antagonists, in combination as a cocktail, with one or more radiolabeled antagonists to these various receptors should very substantially improve the in vivo targeting of such tumors.

Such peptide antagonists are often administered in the form of pharmaceutically or veterinarily acceptable nontoxic salts, such as acid addition salts or metal complexes, e.g., with zinc, iron, calcium, barium, magnesium, aluminum or the like. Illustrative of such nontoxic salts are hydrochloride, hydrobromide, sulphate, phosphate, tannate, oxalate, fumarate, gluconate, alginate, maleate, acetate, citrate, benzoate, succinate, malate, ascorbate, tartrate and the like.

It may also be desirable to deliver these SRIF antagonists over prolonged periods of time, for example, for periods of one week to one year from a single administration, and slow release, depot or implant dosage forms may be utilized as well known in this art. For example, a dosage form may contain a pharmaceutically acceptable non-toxic salt of the compound which has a low degree of solubility in body fluids, for example, an acid addition salt with a polybasic acid; a salt with a polyvalent metal cation; or combination of the two salts. A relatively insoluble salt may also be formulated in a gel, for example, an aluminum stearate gel. A suitable, slow-release depot formulation for injection may also contain an SRIF antagonist or a salt thereof dispersed or encapsulated in a slow degrading, non-toxic or non-antigenic polymer such as a polylactic acid/polyglycolic acid polymer, for example, as described in U.S. Pat. No. 3,773,919.

Therapeutically effective amounts of the peptide antagonists should be administered under the guidance of a physician, and pharmaceutical compositions will usually contain the peptide in conjunction with a conventional, pharmaceutically or veterinarily-acceptable carrier. A therapeutically effective amount is considered to be a predetermined amount calculated to achieve the desired effect. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as earlier described. A therapeutically effective amount is typically an amount of an SRIF antagonist that, when administered peripherally, e.g. intravenously, in a physiologically acceptable composition, is sufficient to achieve a plasma concentration thereof from about 0.1 µg/ml to about 100 µg/ml, preferably from about 1 µg/ml to about 50 µg/ml, more preferably at least about 2 µg/ml and usually 5 to 10 µg/ml. In these amounts, they may be used to desirably affect gastric secretion.

When the composition is to be used for imaging or therapeutic treatments, poor shelf life of the radiolabelled compound and/or the short half-life of the radionuclide may require that the user carry out the labeling reaction with the radionuclide in the clinical hospital or laboratory. In such instances, the various reaction ingredients may be provided to the user in the form of a so-called "kit". The manipulations necessary to perform the desired reaction should be as simple as possible to enable the user to prepare the radioactive labeled composition from the kit using facilities that normally be at one's disposal. Accordingly, a kit for preparing a radiopharmaceutical composition, for detecting and localizing malignant tumors and their metastases in tissues might comprise (i) an SSTR2 selective peptide, an inert pharmaceutically acceptable carrier and/or formulating agent with optional adjuvants, (ii) a solution of a salt or chelate of a radioactive metal isotope, and (iii) instructions for use with a prescription for reacting the ingredients present in the kit.

Preferably, a peptide antagonist to be used as an ingredient of such a kit has been derivatized by a reaction with a chelating agent as defined hereinbefore. The resulting peptide conjugate provides a facility for firmly attaching the radionuclide in a simple manner. Suitable chelating agents for modifying the peptide are described in detail hereinbefore. N-containing di- or polyacetic acids or their derivatives, such as the compounds mentioned before, have proved to be pre-eminently suitable for attaching various metal radionuclides, such as $^{111}$In and $^{113m}$In, to the peptide molecules. The kit to be supplied to the user may also comprise the other ingredients defined above, together with instructions for use, whereas the solution of a salt or chelate of the radionuclide having a limited shelf life, may be supplied to the user separately.

For example, a kit to prepare a radiopharmaceutical composition labeled with $^{99m}$Tc, $^{186}$Re or $^{188}$Re may comprise, in addition to the ingredients defined in (i) and (ii) above, a reducing agent and, if desired, a chelator, and (iii) instructions for use, with a prescription for reacting the ingredients of the kit with $^{99m}$Tc in the form of a pertechnetate solution, or with $^{186}$Re or $^{188}$Re in the form of a perrhenate solution. If desired, various ingredients of the kit may be combined, provided they are compatible. The kit should comprise a reducing agent to reduce the pertechnetate or perrhenate, for example, a dithionite, a metallic reducing agent or a complex-stabilizing reducing agent, e.g. $SnCl_2$, Sn(II)-tartrate, Sn(II)-phosphonate or -pyro-phosphate, or Sn(II)-glucoheptonate. The pertechnetate or perrhenate solution can simply be obtained from a suitable vendor. When the radionuclide is present in the kit itself, the complex-forming reaction with the peptide can simply be produced by combining the components in a neutral medium and causing them to react. For that purpose the radionuclide may be reacted with the peptide in the form of a chelate bound to a comparatively weak chelator, as described hereinbefore.

When the kit comprises a derivatized peptide as defined hereinbefore and is intended for the preparation of a radiopharmaceutical composition, labeled with $^{99m}$Tc, $^{186}$Re or $^{188}$Re, the radionuclide will preferably be added separately in the form of a pertechnetate or perrhenate solution. In that case the kit will comprise a suitable reducing agent and, if desired, a chelator, the former to reduce the pertechnetate or the perrhenate. As a reducing agent may be used, for example, a dithionite or a metallic reducing agent. The ingredients may optionally be combined, provided they are compatible. Such a monocomponent kit, in which the combined ingredients are preferably lyophilized, is excellently suitable for being reacted, by the user, with the radionuclide solution. A metallic reducing agent, for example, Sn(II), Ce(III), Fe(II), Cu(I), Ti(III) or Sb(III); Sn(II), may be used. The peptide constituent of the above-mentioned kits may be supplied as a solution, for example, in the form of a physiological saline solution, or in some buffer solution, but it is preferably present in a dry condition, for example, in the lyophilized condition. When used as a component for an injection liquid it should be sterile, in which, when the constituent is in the dry state, the user should preferably use a sterile physiological saline solution as a solvent. If desired, the above-mentioned constituent may be stabilized in the conventional manner with suitable stabilizers, for example, ascorbic acid, gentisic acid or salts of these acids.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. Although the claims variously define the invention in terms of a peptide sequence, it should be understood that such is intended to include nontoxic salts thereof which are well known to be the full equivalent thereof and which are most frequently administered.

The disclosures of all patents and published patent applications set forth hereinbefore are expressly incorporated herein by reference. As used herein, all temperatures are ° C. and all ratios are by volume. Percentages of liquid materials are also by volume.

Various features of the invention are emphasized in the claims which follow.

The invention claimed is:

1. A cyclic somatostatin(SRIF) peptide antagonist which selectively binds the SRIF receptor SSTR2 without triggering internalization into a cell, which peptide comprises:

the amino acid sequence (cyclo3-14)$Xaa_1$-$Xaa_2$-D-$Xaa_3$-$Xaa_4$-$Xaa_5$-$Xaa_6$-$Xaa_7$-$Xaa_8$-$Xaa_9$$Xaa_{10}$-$Xaa_{11}$-$Xaa_{12}$-$Xaa_{13}$- $Xaa_{14}$-$Xaa_{15}$ wherein:

$Xaa_i$ is des-Xaa;

$Xaa_2$ is Trp(A), Phe(B), Nal or Tyr, where A is H, Cl, F, Br, Me, $NO_2$, OMe or N-formyl and B is H, halogen, $CH_3$, $NO_2$, or $OCH_3$;

D-$Xaa_3$ is D-Cys, D-Pen, D-HCys or another D-isomer α-amino acid having an SH-side chain;

$Xaa_4$, $Xaa_5$ and $Xaa_6$ are des-Xaa;

$Xaa_7$ is Aph($Q_1$), Tyr(X), Ala(thienyl) or Trp(A) where $Q_1$ is Cbm, OH-Cbm, $CH_3$-Cbm, $OCH_3$-Cbm, OEt-Cbm, Cbm-Et$(OEt)_2$ or Hor, A is H, Cl, F, Br, Me, $NO_2$, OMe or N-formyl, and where X is H or halogen;

$Xaa_8$ is Trp(5F), Trp(5Cl), Trp(5Br), Trp(5Me), Trp (5OMe), Trp(6F), Trp(6Cl), Trp(6Br), D-Trp(5F), D-Trp(5Cl), D-Trp(5Br), D-Trp(5Me), D-Trp (5OMe), D-Trp(6F), D-Trp(6Cl), D-Trp(6Br), Tyr,

D-Tyr, Phe(B), D-Phe(B), L or D-BzlHis, L or D-(DNP)His, L or D-Aph(Cbm);

Xaa$_9$ is Lys, N$^\alpha$MeLys, hLys, N$^\alpha$MehLys, Orn or N$^\alpha$Me-Orn;

Xaa$_{10}$ is Thr, Ser or Val;

Xaa$_{11}$, Xaa$_{12}$ and Xaa$_{13}$ are des-Xaa;

Xaa$_{14}$ is Cys, Pen, hCys or another L- isomer α-amino acid having an SH side chain; and Xaa$_{15}$ is 2Nal, D-2Nal, Aph(Q$_2$), D-Aph(Q$_2$), (R$_1$)Cha, (R$_1$)D-Cha, (R$_1$)Leu, (R$_1$)D-Leu, Tyr, D-Tyr, Trp, D-Trp or des-Xaa; where R$_1$ is H or C$^\alpha$Me, and Q$_2$ is Cbm, OH-Cbm, CH$_3$-Cbm, OCH$_3$-Cbm or OEt-Cbm.

2. The peptide according to claim 1 wherein Xaa$_7$ is Aph (Q$_1$), Ala(thienyl) or Trp(A) and D-Xaa$_3$ is D-Cys.

3. The peptide according to claim 1 wherein Xaa$_7$ is Aph (Hor), Aph(Cbm), Tyr or ITyr.

4. The peptide according to claim 1 wherein Xaa$_8$ is selected from the group consisting of Trp(5F), Trp(5Cl), Trp (5Br), Trp(5Me), Trp(5OMe), Trp(6F), Trp(6Cl), Trp(6Br), D-Trp(5F), D-Trp(5Cl), D-Trp(5Br), D-Trp(5Me), D-Trp (5OMe), D-Trp(6F), D-Trp(6Cl), D-Trp(6Br), and D-Aph (Cbm).

5. The peptide according to claim 1 wherein Xaa$_7$ is Aph (Hor), Xaa$_8$ is D-Aph(Cbm) and Xaa$_{15}$ is 2Nal or D-Tyr.

6. The peptide according to claim 1 wherein Xaa$_2$ is Phe(B) where B is Cl; Xaa$_7$ is Aph(Hor); Xaa$_8$ is D-Aph(Cbm); Xaa$_9$ is Lys; and Xaa$_{15}$ is 2Nal or D-Tyr.

7. The peptide according to claim 1 wherein Xaa$_2$ is 4Cl (Phe) or 4NO$_2$(Phe).

8. The peptide according to claim 1 wherein Xaa$_2$ is 4Cl (Phe) or 4NO$_2$(Phe); Xaa$_7$ is Tyr(X); Xaa$_8$ is D-Aph(Cbm) or D-Trp(A); and Xaa$_{15}$ is 2Nal or D-Tyr.

9. The peptide according to claim 1 wherein there is also present at the N-terminus a moiety Z which is a chelator, a complexing agent, a conjugating agent or a label.

10. The peptide according to claim 9 wherein Z is selected from the group consisting of DOTA- and DTPA-based chelators, NOTA-based chelators, carbonyl compounds, 2hydrazino nicotinamide, N$_4$-chelators, desferrioxamin, and N$_x$S$_y$-chelators and wherein said moiety Z is optionally attached to Xaa$_2$ by a linker L.

11. A pharmaceutical composition comprising a mixture of the peptide according to claim 1 and at least one pharmaceutically acceptable carrier.

12. A cyclic somatostatin(SRIF) analog peptide which selectively binds the SRIF receptor SSTR2, which peptide comprises:

the amino acid sequence cyclo(3-14)Xaa$_1$-Xaa$_2$-D-Cys-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Cys-Xaa$_{15}$-NH$_2$ wherein:
Xaa$_1$ is des-Xaa;
Xaa$_2$ is chloro or nitro Phe;
Xaa$_4$, Xaa$_5$ and Xaa$_6$ are des-Xaa;
Xaa$_7$ is Aph(Hor), Tyr or ITyr;
Xaa$_8$ is D-Aph(Cbm);
Xaa$_9$ is Lys, Orn, hLys, N$^\alpha$MeLys or N$^\alpha$MeOrn;
Xaa$_{10}$ is Thr;
Xaa$_{11}$, Xaa$_{12}$ and Xaa$_{13}$ are des-Xaa; and
Xaa$_{15}$ is 2Nal or D-Tyr.

13. The peptide according to claim 12 wherein there is attached to Xaa$_2$ a moiety (Z) selected from the group consisting of DOTA-based chelators, DTPA-based chelators, NOTA-based chelators, carbonyl compounds, 2hydrazino nicotinamide, N$_4$-chelators, desferrioxamin, and N$_x$S$_y$-chelators.

14. The peptide according to claim 13 wherein Xaa$_2$ is 4Cl(Phe) or 4NO$_2$(Phe) and a DOTA chelator is covalently attached thereto.

15. A peptide which has one of the following amino acid sequences wherein the C-terminus is amidated:

Cpa-cyclo[D-Cys-4Aph(Hor)-D-Aph(Cbm)-Lys-Thr-Cys]-2Nal;

Cpa-cyclo[D-Cys-4Aph(Cbm)-D-Trp-Lys-Thr-Cys]-2Nal;

pNO$_2$-Phe-cyclo[D-Cys-Tyr-D-Aph(Cbm)-Lys-Thr-Cys]-2Nal;

Cpa-cyclo[D-Cys-Tyr-D-Aph(Cbm)-Lys-Thr-Cys]-2Nal;

pNO$_2$-Phe-cyclo[D-Cys-ITyr-D-Trp-Lys-Thr-Cys]-D-Tyr;

pNO$_2$-Phe-cyclo[D-Cys-Tyr-D-Aph(Cbm)-Lys-Thr-Cys]-D-Tyr; and

Cpa-cyclo[D-Cys-4Aph(Hor)-D-Aph(Cbm)-Lys-Thr-Cys]-D-Tyr.

* * * * *